United States Patent [19]

Characklis

[11] Patent Number: 4,521,864
[45] Date of Patent: Jun. 4, 1985

[54] MEASUREMENT OF BUILD-UP OF FOULING DEPOSITS BY SENSING FLOW CHARACTERISTICS DURING BRIEF FLOW EXCURSIONS

[76] Inventor: William G. Characklis, 516 W. Cleveland St., Bozeman, Mont. 59715

[21] Appl. No.: 429,254

[22] Filed: Sep. 30, 1982

[51] Int. Cl.³ .................. G01N 11/04; G01B 13/10
[52] U.S. Cl. .................................. 364/563; 73/61.2
[58] Field of Search ............... 364/509, 510, 563; 73/61 R, 61.2

[56] References Cited

U.S. PATENT DOCUMENTS

| | | | |
|---|---|---|---|
| 3,552,189 | 1/1971 | Courvoisier et al. | 73/61.2 |
| 4,059,744 | 11/1977 | Elderton | 364/510 X |
| 4,176,544 | 12/1979 | Eyles et al. | 73/61.2 |
| 4,247,899 | 1/1981 | Schiller et al. | 364/510 X |

Primary Examiner—Errol A. Krass
Assistant Examiner—Edward R. Cosimano
Attorney, Agent, or Firm—Eric P. Schellin

[57] ABSTRACT

A method and apparatus for measuring the thickness of film fouling in a hydraulic system. While the system is clean and unfouled, it is subjected to a brief test run during which the water velocity is swept over a wide range and the corresponding pressure drops are measured and recorded to provide a reference curve for the velocity-pressure drop characteristic. Later, when the system is fouled, the brief test run is repeated to arrive at a new reference curve, part of which substantially coincides with the said reference curve and part of which departs monotonically. The point of departure, by calculation, yields the thickness of the film fouling.

3 Claims, 4 Drawing Figures

FIG. 1
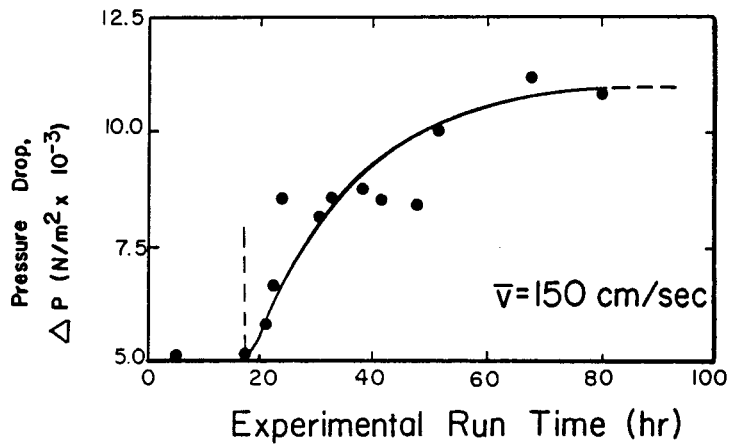
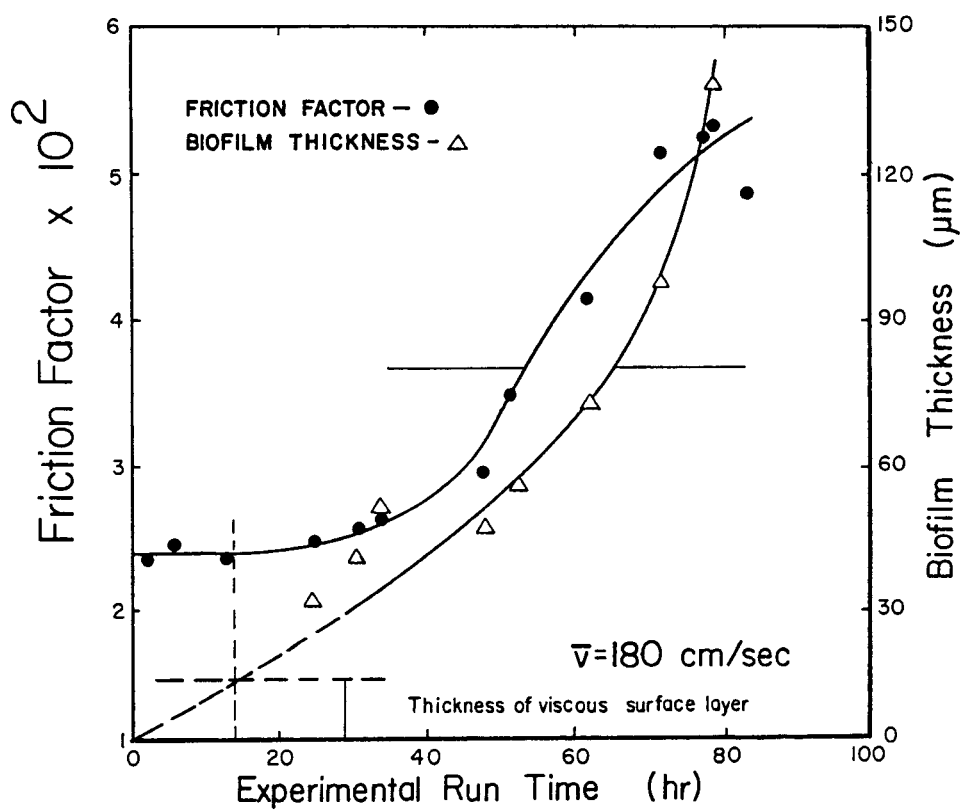
FIG. 2

MEASUREMENT OF BUILD-UP OF FOULING DEPOSITS BY SENSING FLOW CHARACTERISTICS DURING BRIEF FLOW EXCURSIONS

RELATED APPLICATIONS

Copending application Ser. No. 259,466, by William G. Characklis et al, filed May 1, 1981, for a Method and Apparatus for Determining the Heat Transfer Characteristics of a Tube, now U.S. Pat. No. 4,396,300, granted Aug. 2, 1983, relates to a system for determining the growth of fouling deposits by measurement of the changing heat transfer characteristics of the tube.

Copending application Ser. No. 338,972, by William G. Characklis, filed Sept. 30, 1982, for Monitoring Build-up of Fouling Deposits on Surfaces of Fluid Handling Systems, now U.S. Pat. No. 4,485,450, granted Nov. 27, 1984 relates to a system for determining the growth of fouling deposits by measurement of the changing torque required to drive a rotor, and to the computer control and recording system associated therewith.

SUMMARY

The measurement of the thickness of build-up of a fouling layer on the inner wall of a tube, in which a fluid flows, is difficult. The build-up is frequently biological and slime-like in character, and is not susceptible of direct measurement by simple geometric means. In the past, the thickness has been measured indirectly by various methods. For example, the difference in weight of a section of tube, when freshly removed from the circulating fluid system, and when thoroughly drained and dried, would be closely related to the weight of fluid held in the fouling layer, and this weight could be converted, by calculation, into the thickness of the fouling layer.

The invention described herein permits the indirect measurement of the thickness of the fouling layer without removal of or intrusion into any section of the circulating fluid system.

The measurement depends upon the fact that a smooth tube continues to act as a smooth tube, despite build-up of a fouling layer, until the peaks of the irregular fouling layer start to project through a viscous sublayer (i.e., a boundary layer) which exists adjacent to the inside wall of the smooth tube. When the said peaks start to stick out above the viscous surface layer, then the tube starts to assume the characteristics of a rough tube.

Thus, if the flow rate in the tube is subject to a brief flow excursion, the viscous sublayer will increase or decrease and the onset of evidence of increased fluid friction over that of a clean smooth tube can be detected, and the rate of flow and pressure drop for said onset can be used to calculate the thickness of the fouling layer.

Although fouling is frequently biological in nature, it can also be caused by chemical and physical processes operating on salts, minerals, corrosion products and sediment. The invention described herein permits measurement of the thickness of non-biological fouling deposits, as well as the thickness of biological fouling deposits.

THE DRAWINGS

FIG. 1 is a graph showing the pressure drop in a tube through which fluid flows, plotted against the duration of the run.

FIG. 2 is a double graph of friction factor and biological film thickness, plotted against the duration of the run of fluid through a tube.

DETAILED DESCRIPTION

Figure 3:
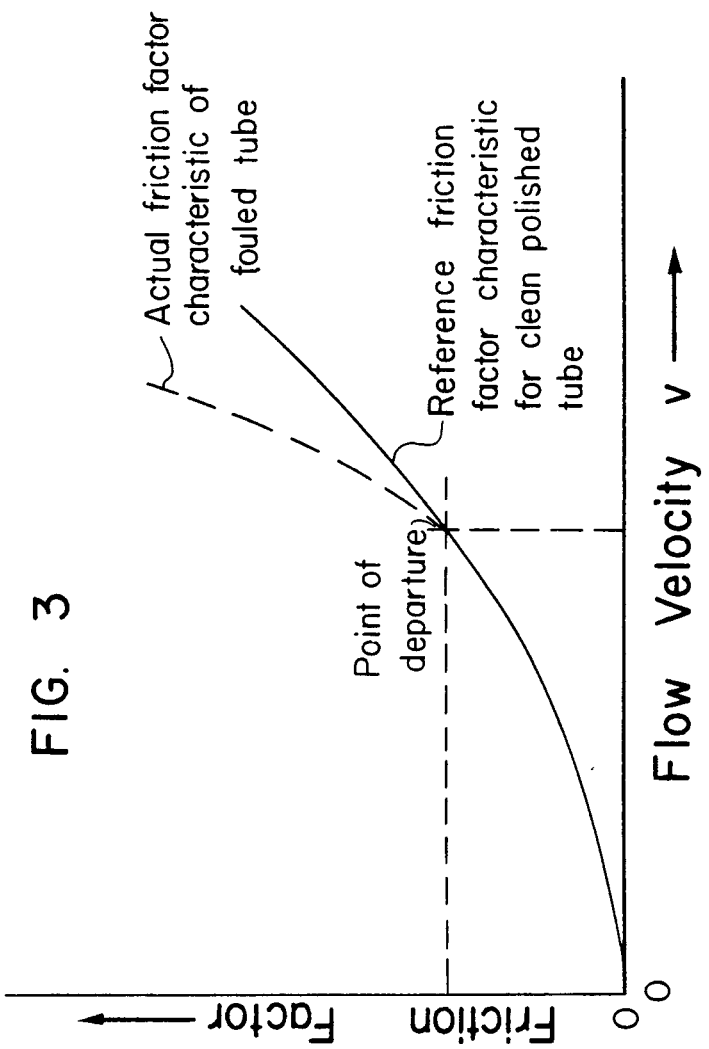
FIG. 3 is a double graph of friction factor for a clean and for a fouled tube, plotted against the flow velocity.

The flow of fluid in a circular tube can be described in terms of a dimensionless friction factor f as follows:

$$f = 2d/L \cdot \Delta P \cdot 1/\rho \cdot v^2 \qquad (1)$$

where d and L are the diameter and length of a straight section of the tube, $\Delta P$ is the pressure drop along said straight section, $\rho$ is the fluid density and $v$ is the fluid velocity, averaged across the tube cross section.

The valve of the friction factor f does not stay constant with passage of time, because the inside wall of the tube gradually becomes covered with an accreting coating of fouling deposits. The fouling impedes the flow of fluid, thereby increasing the value of f.

FIG. 1 is a plot of the pressure drop along a section of tube plotted against the elapsed time that fluid has been flowing through the tube. The bore of the tube was clean and polished at the start of the experimental run at time equals zero. It will be noted that from time equals zero to about time equals 18 hours the pressure drop is constant. At time equals 18 hours the pressure drop starts to increase monotonically with increasing time.

The explanation for the change of behavior which occurs at time equals 18 hours is that in a clean tube there is a viscous sublayer of fluid which seemingly sticks to the inner tube walls, so that the longitudinal flow in said layer is extremely small, compared to the flow in the main body of the tube. During the first 18 hours, the fluid flow occurring in the tube can be considered to take place, not in the bore of the tube, as defined by its inner diameter, but in a smaller bore, defined by the inner diameter of the viscous sublayer. When the fouling deposits are so slight that the peaks thereof do not project through the thickness of the viscous sublayer, the fouling does not affect the flow. When the fouling deposits increase in size so as to project above the viscous sublayer, then the deposits will impede the flow of fluid. After the peaks of the fouling deposits project above the viscous sublayer, the deposits hinder the flow of fluid to an extent much greater than to be expected from the mere reduction of cross-sectional area of the flow channel through the tube. This indicates that the roughness associated with the fouling deposits is predominant in restricting flow.

FIG. 2 shows the results of a different experimental run in which, in addition to the friction factor f, the thickness of the fouling deposit was measured. Both quantities are plotted against elapsed time of the experiment. It will be noted that the friction factor f stays constant till about 14 hours, at which time it begins to increase monotonically with time. The thickness of the fouling also increases monotonically with time. While the thickness cannot be readily measured when the fouling is very thin, it is to be taken for granted that the thickness is zero when the run is started with a clean tube, and accordingly the lower end of the thickness graph has been extrapolated to run through zero. In FIG. 2 the left abscissa is measured in terms of friction rather than pressure drop, but these two quantities are directly proportional to each other by the equation (1). Accordingly, FIG. 2, for the friction factor curve, illustrates the same phenomena as does FIG. 1. Namely, an initial period of constant resistance to fluid flow is followed by a period where the resistance to fluid flow increases.

It will be noted that in FIG. 2, the friction factor exhibits an upward trend after about 14 hours, which is a different time lapse than the corresponding one of FIG. 1. This is because the run conditions, particularly the average fluid velocity $v$, were different in FIGS. 1 and 2. However, for the particular run of FIG. 2, the time of 14 elapsed hours can be used to conclude, by following the dotted lines, that the thickness of the fouling deposit (which at 14 hours was also the thickness of the viscous surface layer) was about 13 micrometers.

A large number of experimental runs of the type depicted in FIG. 2, with various parameters varied, lead to the following empirical formula for the thickness of the viscous: subsurface $$\delta = 10d/R \cdot v\sqrt{f/2} \qquad (2)$$

where $\delta$ is the said thickness, d is the diameter of the bore of the tube, R is the Reynolds number and f is the friction factor.

The invention described herein rests on the realization that in an experimental run to determine the rate of fouling, the flow rate can be increased or decreased for a brief excursion to the required extent whereat apparatus for measuring flow resistance detects the beginning of a departure of resistance from that measured for similar flow at the start of the experiment with a clean tube. The steady state conditions of the experiment are immediately reestablished, but the friction factor measured at the moment of said departure can be used, by means of equation (2), to calculate the thickness of the fouling layer.

This is illustrated in FIG. 3. The fouling run commences at time zero where, for a brief excursion, the data for the solid line characteristic for a clean tube is obtained by varying the flow rate over a wide range. Then, for periods of perhaps two hours the experiment operates in its steady state flow rate, during which fouling slowly builds up. Between each of the two hour periods there is a brief excursion in which the flow rate is swept over a suitable range during which the then friction characteristic shown by the dashed graph is observed. The point of departure of the dashed characteristic from the solid characteristic is readily determined and the corresponding friction factor, by equation (2), yields the thickness of the viscous subsurface, which is also the thickness of the fouling deposit.

The information involved in the measurement of the thickness of the fouling deposits by the above-discussed technique is susceptible of being automatically measured and processed by a computer during the run of an experiment.

Figure 4:
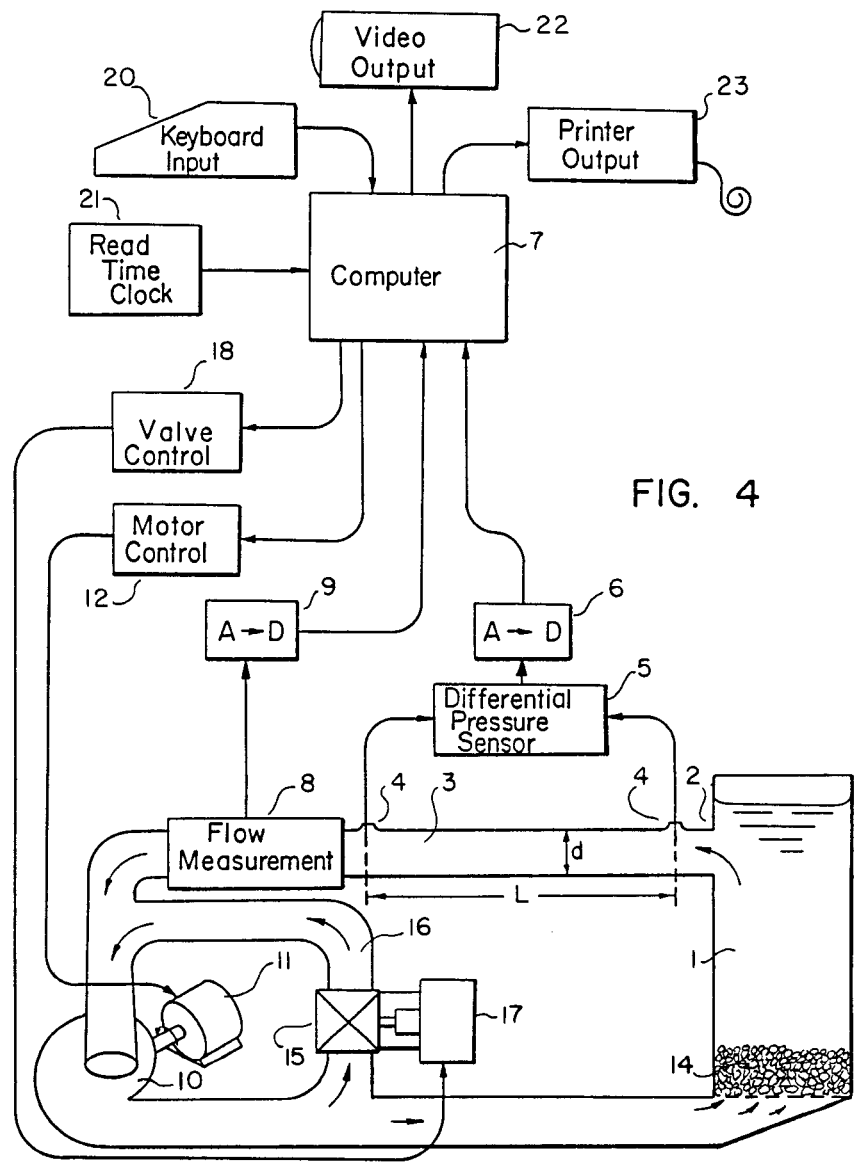
FIG. 4 is a dragram of an embodiment of the instant invention.

An illustrative embodiment is seen in FIG. 4. A reservoir 1 supplies water to a straight and uniform tube 2 having a test section 3 of length L and diameter d, as indicated by legends. At each end of the test section 3 sensing means 4 are situated to respond to the water pressure at the respective ends. The sensing means 4 are connected to a differential pressure sensor 5 which outputs an analog signal, indicative of the difference in pressure at the two ends of the test section 3, into analog to digital converter 6. Converter 6 then feeds the pressure differential data to computer 7.

Downstream of the test section a flow responsive sensor 8 measures the flow coming from the test section 3. The analog signal from flow responsive sensor 8 is inputted into analog to digital converter 9, which in turn feeds the flow data to computer 7.

The fluid flowing through test section 3 and flow responsive sensor 8 goes to pump 10, driven by motor 11. The speed of motor 11 is regulated by motor control 12, as commanded by computer 7.

The pump 10 impells the flow fluid back to the reservoir 1 by way of a turbulence reducing diffuser 14.

The velocity of the flowing fluid can be determined not only by the speed of the motor 11 which turns pump 10, but also by the degree to which valve 15, situated in by-pass 16, is opened or closed by valve actuator 17. Valve actuator 17 is regulated by valve control 18, as commanded by computer 7.

The combination of a variable speed motor 11 for pump 10 and a variable valve 15 for by-pass 16 has advantage over the use of either one alone in that it is possible to more economically obtain control of the fluid flow over a wide range of velocities.

If it is desired to operate the hydraulic circuit in steady state manner, the set-up is as follows:

The keyboard 20 is operated to indicate to the computer 7 the desired mode of operation, namely, (a) constant pressure drop over the length L of the test section 3 or (b) constant velocity $v$ of the flow through the test section 3. Since the test section 3, during the course of the run, will become impeded with a layer of fouling deposit, it follows that option (a) requires a decreasing flow as time goes on and option (b) requires an increasing pressure drop as time goes on.

The keyboard 20 is further operated to indicate to the computer at what intervals of time, as given by read time clock 21, the dependent variable (decreasing flow in alternative (a) and increasing pressure drop in alternative (b) is to be measured, stored in the computer 7, displayed in the video output 22 and printed in the printer output 23.

It will be evident to those skilled in the art that the computer 7, when programmed by keyboard input 20 for the desired task, acts as part of a feedback system which keeps either the measured pressure drop constant in alternative (a) or the measured fluid flow constant in alternative (b).

For example, in alternative (a) at the beginning of each measurement period, as determined by read time clock 21 and the set-up input from keyboard input 20, the momentary output of analog to digital converter 6 is stored in computer 7 and the said stored value is compared to the reference value, also stored in computer 7 (from the original set-up on keyboard 20) of the desired steady state value. If the difference is zero, the measured pressure drop is what is desired, and the computer commands no change in either the motor control 12 or the valve control 18.

If the difference is, say, negative, the computer could command the motor control 18 to make the motor 11 run faster and/or the valve control 18 to make the valve 15 close somewhat, and vice-versa if the difference is positive. The amount of faster running or valve closing could be the minimum achievable increment, or it could be an amount proportional to the said difference or it could be an amount determined by feedback system dead-beat non-hunting requirements, as will be understood by those skilled in feedback systems.

Just as the system of FIG. 4 can be programmed for steady state running, so can it also be programmed for a brief excursion, say 5 minutes long, at the beginning of every interval of, say, two hours.

In order to measure the fouling deposit build-up, the computer is programmed to vary the velocity $v$ of the flow over a wide sweep during the excursion, and to store simultaneous readings of pressure drop and current velocity (as delivered to computer 7 from analog to digital converters 6 and 9). These stored readings in the computer 7 correspond to the "reference friction characteristic for a clean tube" of FIG. 3. Immediately after the brief excursion, the hydraulic system is restored to steady state condition. After an interval of two hours, and every two hours thereafter, the hydraulic system is subjected to another similar excursion in its flow velocity $v$. During a subsequent excursion, the computer will be able to sense the flow velocity $v$ at which the actual friction characteristic during said subsequent excursion departs from the reference friction characteristic. The computer then uses its stored data to compute the thickness $\delta$ of the fouling layer by use of equation (2), and prints out the data on acretion of the fouling deposit. As time goes on and the fouling deposit grows thicker, the velocity $v$ at which the departure is noticed becomes smaller with each subsequent excursion.

The system of FIG. 4 has been described as being a dedicated experimental system. However, this is merely illustrative. If fact, the same kind of automatic sensing and recording of acretion of biological fouling deposits can take place in other environments, merely by adding a few controls, sensing means and a computer.

For example, a cooling tower system already has portions which correspond exactly to reservoir 1, tube 2, test section 3, pump 10 and motor 11. Thus, the cost of adding the other items seen in FIG. 4 is small compared to the cost of the cooling tower system, and the invention, as described above, is directly applicable to cooling tower systems.

Furthermore, the invention is not restricted to systems having an individual circulating pump, such as pump 10. It can also be used where the fluid pressure is supplied by some larger system. The larger system may have a pump of its own, or the larger system may be a gravity propelled fluid system. In either case, a motorized valve, controlled by a computer, in turn controls the flow excursion.

The method is not restricted to use in pumped systems. The flow can be driven by gravity forces as well.

The method is not restricted to measuring the thickness of deposits of biological origin. The method is capable of measuring deposit thickness of chemical deposits, corrosion deposits, and sedimentation deposits or their combination.

The viscous sublayer referred to in this description is also termed the boundary layer in fluid mechanical terminology.

What is claimed is:

1. The method of determining the thickness of a fouling deposit in a hydraulic conduit of uniform cross section which comprises the steps of:

determining, for a test section of said conduit, while in a clean and polished condition, the relationship between fluid flow velocity and fluid pressure drop over a wide range of fluid flow velocities;

recording said relationship to establish, for later use, a reference characteristic;

using said conduit for a period of time during which the conduit becomes coated with a fouling deposit;

at the end of said period of time determining, for said test section, while in its then fouled condition, the relationship between fluid flow velocity and fluid pressure drop over a wide range of fluid flow velocities;

recording said relationship to establish, for the time of the test, a transitory test characteristic;

comparing said reference characteristic with said transitory test characteristic to determine the critical fluid velocity below which the two characteristics are substantially identical and above which they diverge; and utilizing said critical fluid velocity as a measurement to determine the thickness of the fouling deposit in said conduit at said time of the test.

2. A system for determining the thickness of a fouling deposit in a hydraulic conduit of uniform cross section which comprises:

a test section of said conduit;

means for measuring the fluid pressure drop along said test section and the fluid rate through said test section;

fluid propelling means for establishing a desired steady state hydraulic condition in said test section for the duration of a fouling test run;

said fluid propelling means, when so commanded, also subjecting the fluid flow rate to a brief excursion over a wide range of flow rates;

means for commanding said fluid propelling means to perform said brief excursion at the beginning of said fouling test run when the conduit is unfouled and for, at a later time, when the conduit is fouled, again commanding said fluid propelling means to perform another similar, but later in time, brief excursion;

said fluid propelling means maintaining said desired steady state hydraulic condition at all times except when so commanded;

means for storing the fluid pressure drop and fluid flow rate measurements taken at the beginning of said fouling test run to preserve the fluid pressure drop versus fluid flow rate characteristic for the unfouled conduit and for similarly storing the same measurements taken at said later time to preserve the fluid pressure drop versus fluid flow rate characteristic for the fouled conduit;

means for comparing the two said characteristics to determine the critical fluid flow rate below which the two characteristics substantially coincide and above which they monotonically diverge; and means for computing the thickness of the fouling deposit at said later time from the value of said critical flow rate.

3. The system of claim 2 having a digital computer;

said digital computer having time clock which times the sequential operation of said digital computer;

said fluid propelling means and said means for commanding said fluid propelling means being under the control of signals sent by said digital computer;

said means for storing the fluid pressure drop and fluid flow rate measurements being the data store of said digital computer; and said means for comparing being the arithmetic-logic unit of said digital computer.

* * * * *